「(12) United States Patent
Takita et al.

(10) Patent No.: US 9,249,258 B2
(45) Date of Patent: Feb. 2, 2016

(54) METHOD FOR PRODUCING POLY-3-HYDROXYALKANOIC ACID AND AGGLOMERATES THEREOF

(75) Inventors: Masaki Takita, Takasago (JP); Yoshifumi Yanagita, Takasago (JP)

(73) Assignee: Kaneka Corporation, Osaka (JP)

( * ) Notice: Subject to any disclaimer, the term of this patent is extended or adjusted under 35 U.S.C. 154(b) by 222 days.

(21) Appl. No.: 13/133,610

(22) PCT Filed: Dec. 2, 2009

(86) PCT No.: PCT/JP2009/006546
§ 371 (c)(1),
(2), (4) Date: Aug. 12, 2011

(87) PCT Pub. No.: WO2010/067543
PCT Pub. Date: Jun. 17, 2010

(65) Prior Publication Data
US 2011/0293938 A1    Dec. 1, 2011

(30) Foreign Application Priority Data
Dec. 9, 2008    (JP) ................................ 2008-313331

(51) Int. Cl.
C08G 63/06 (2006.01)
C08G 63/88 (2006.01)
C08G 63/90 (2006.01)
C08J 3/14 (2006.01)
C12P 7/62 (2006.01)

(52) U.S. Cl.
CPC ............... *C08G 63/06* (2013.01); *C08G 63/88* (2013.01); *C08G 63/90* (2013.01); *C08J 3/14* (2013.01); *C12P 7/625* (2013.01); *C08J 2367/04* (2013.01); *Y10T 428/2982* (2015.01)

(58) Field of Classification Search
CPC ............ C08G 63/06; C08G 63/90; C08J 3/14
See application file for complete search history.

(56) References Cited

U.S. PATENT DOCUMENTS

| | | | | |
|---|---|---|---|---|
| 5,334,520 | A | * | 8/1994 | Dennis ........................ 435/136 |
| 5,798,440 | A | | 8/1998 | Liddell et al. |
| 7,393,668 | B2 | * | 7/2008 | Yanagita et al. ............... 435/135 |
| 2003/0186398 | A1 | * | 10/2003 | Schumann et al. ........... 435/135 |
| 2005/0196827 | A1 | | 9/2005 | Osakada et al. |
| 2007/0161096 | A1 | | 7/2007 | Mantelatto et al. |
| 2008/0118963 | A1 | * | 5/2008 | Ogawa et al. .................. 435/142 |

FOREIGN PATENT DOCUMENTS

| | | |
|---|---|---|
| EP | 1609868 A1 | 12/2005 |
| JP | 07-079788 | 3/1995 |
| JP | 07-102053 A | 4/1995 |
| JP | 07-509131 | 10/1995 |
| JP | 8-502415 | 3/1996 |
| JP | 10-504460 | 5/1998 |
| JP | 11-266891 | * 10/1999 |
| JP | 2000-502399 | 2/2000 |
| JP | 2000-503046 | 3/2000 |
| JP | 2002-517582 | 6/2002 |
| JP | 2005-348640 | 12/2005 |
| JP | 2007-512007 A | 5/2007 |
| WO | WO-94/10289 | 5/1994 |
| WO | WO-96/06179 | 2/1996 |
| WO | WO-97/22654 | 6/1997 |
| WO | WO-97/23549 | 7/1997 |
| WO | WO-99/64498 | 12/1999 |
| WO | WO-2004/065608 | 8/2004 |
| WO | WO-2005/085461 | 9/2005 |

OTHER PUBLICATIONS

Volume Editor: Rehm, Hans-Jurgen, edited by Rehm, H-J. and Reed, G., Chapter 6 Microbial Production of Poly-β-Hydroxybutyric Acid, Biotechnology (A comprehensive Treatise in 8 Volumes), vol. 6b (Special Microbial Processes), VCH Verlagsgesellschaft, 1988, p. 136-176.
Supplemental European Search Report issued Dec. 23, 2014 in EP Appln No. 09831651.

* cited by examiner

*Primary Examiner* — Gregory Listvoyb
(74) *Attorney, Agent, or Firm* — Novak Druce Connolly Bove + Quigg LLP

(57) ABSTRACT

When industrially separating and purifying poly-3-hydroxyalkanoic acid produced by a microorganism, to obtain poly-3-hydroxyalkanoic acid agglomerates having an arbitrary volume mean particle diameter with favorable productivity and with decreased amount of an organic solvent used is enabled while decreasing contaminants derived from constitutive components of cellular bodies. According to the present invention, agglomerates of poly-3-hydroxyalkanoic acid are obtained by adjusting the pH of an aqueous poly-3-hydroxyalkanoic acid suspension to fall within an acidic region.

15 Claims, No Drawings

METHOD FOR PRODUCING POLY-3-HYDROXYALKANOIC ACID AND AGGLOMERATES THEREOF

CROSS REFERENCE TO RELATED APPLICATIONS

This application is a National Phase filing under 35 U.S.C. §371 of PCT/JP2009/006546 filed on Dec. 2, 2009; and this application claims priority to Application No. 2008-313331 filed in Japan on Dec. 9, 2008 under 35 U.S.C. §119; the entire contents of all are hereby incorporated by reference.

TECHNICAL FIELD

The present invention relates to a method for forming poly-3-hydroxyalkanoic acid agglomerates from an aqueous suspension of poly-3-hydroxyalkanoic acid, and agglomerates obtained therefrom.

BACKGROUND ART

Poly-3-hydroxyalkanoic acid (hereinafter, abbreviated as PHA) is a thermoplastic polyester produced and accumulate in cells of many microorganism species as an energy storage material, and has biodegradability. At present, non-petroleum plastics have attracted attention owing to increased environmental consciousness. In particular, biodegradable plastics such as PHA which are incorporated in material recycling in the natural world and thus the degradation products do not become harmful have drawn attention, and to put them into practical applications has been desired. Particularly, since PHA formed and accumulated by microorganisms in cellular bodies is incorporated into the process of carbon cycle of the natural world, lower adverse effects on the ecological system have been expected.

Since PHA produced by a microorganism usually forms a granular body and is accumulated in the cellular bodies of the microorganism, a step of separating and recovering PHA from inside the cellular bodies of the microorganism is necessary for utilizing PHA as a plastic. In addition, for using PHA as a plastic, it is desired to increase the purity of PHA, and to lower the content of contaminants of constitutive components and the like of cellular bodies, and the like.

As a method for degradation and/or removal of components other than PHA derived from an organism, a method in which components other than PHA derived from an organism are solubilized and removed by a physical treatment, a chemical treatment or a biological treatment was proposed. For example, a method in which a treatment of disrupting cellular bodies of a PHA-containing microorganism and a treatment with a surfactant are combined (Patent Document 1), a method in which a heat treatment after adding an alkali is followed by carrying out a disruption treatment (Patent Document 2), and the like may be exemplified. In addition, a method for obtaining PHA in which aqueous suspension of cellular bodies of a microorganism is subjected to a treatment with sodium hypochlorite or an enzyme to solubilize components other than PHA derived from an organism (Patent Document 3) was also proposed.

Also, as a means for recovering PHA from an aqueous suspension obtained by disrupting cellular bodies of a PHA-containing microorganism or solubilizing components other than PHA derived from an organism, separating operation such as centrifugation or filtration, or drying operation such as spray drying may be exemplified. However, when PHA particles produced by cellular bodies are directly recovered as primary particles, fine powders increase, and thus a problem of handling as a product to be difficult may be involved.

It is generally known that addition of a salt or the like enables solid powders in a fine slurry solid-liquid dispersion liquid to be aggregated. However, it is extremely difficult to allow only target PHA to be aggregated from an aqueous suspension containing cellular components leaked from disrupted cells, such as proteins in addition to PHA, and there has been no example of such findings. Even if aluminum sulfate, which has been widely used in activated sludge treatments, etc., or the like is used, it is impossible to allow only target PHA to be selectively aggregated since almost all components in the aqueous suspension are aggregated. In addition, even if PHA can be selectively aggregated with a polymeric coagulant or the like, quality as a polymer material may be affected since separating these additives from PHA is difficult.

As a method conducted without using a coagulant, a method in which a PHA suspension is heated (Patent Document 4), a method in which heating and cooling are repeated (Patent Document 5), and the like have been known. In any of the methods, lowering of the molecular weight of PHA upon heating has been concerned since heating to around the melting point of PHA is carried out.

On the other hand, a method in which after PHA is dissolved in an organic solvent, an organic solvent having low solubility or water is added thereto to allow thus dissolved PHA to be deposited has been known. Since a PHA solution can be purified according to this method, it has enabled to obtain PHA having a highest purity. As such a solvent extraction method, an example in which a lower ketone or the like is used as an extraction solvent (Patent Document 6), an example in which tetrahydrofuran is used (Patent Document 7) and the like were reported. If a poor solvent is added to an organic solvent including PHA dissolved therein, deposition of PHA is enabled, and it has been possible to comparatively arbitrarily control the shape and size of the deposit, depending on the solvent to be added, and conditions of addition such as a temperature and amount of addition, as well as stirring conditions during the addition, and the like.

The capability of controlling the shape and size of the deposited matter by thus allowing PHA to be deposited from an organic solvent has been very advantageous in view of problems of PHA purified using a water soluble solvent that it includes a large amount of fine powders. However, this process has involved fundamental problems of: use of a large quantity of organic solvent in extraction; lowering of the molecular weight of PHA during the purification step as PHA originally being highly degradable is heated for dissolving the same; and the like.

Accordingly, when PHA produced by a microorganism is industrially separated and purified, there have been problems of failure in obtaining PHA particles having an arbitrary volume mean particle diameter with favorable productivity while decreasing contaminants derived from constitutive components of cellular bodies, taking into consideration the environmental aspects. Furthermore, since the parameter dominating over agglomeration of PHA particles has been unclear, it has been still further difficult to propose means for solving these problems.

PRIOR ART DOCUMENT

Patent Document

Patent Document 1: JP-T No. H08-502415
Patent Document 2: PCT International Publication No. 2004/065608
Patent Document 3: JP-A No. 2005-348640
Patent Document 4: JP-T No. 2000-502399
Patent Document 5: JP-T No. 2002-517582
Patent Document 6: JP-T No. H10-504460
Patent Document 7: JP-A No. H07-79788

DISCLOSURE OF THE INVENTION

Problems to be Solved by the Invention

Problems to be solved by the present invention is, when industrially separating and purifying PHA produced by a microorganism, to obtain PHA particles having an arbitrary volume mean particle diameter with favorable productivity and with decreased amount of an organic solvent used while decreasing contaminants derived from constitutive components of cellular bodies, without adding a salt, a polymeric coagulant or the like, and also without carrying out a high temperature treatment.

Means for Solving the Problems

The inventors found that PHA is aggregated without addition of a salt, a polymeric coagulant or the like, at a comparatively low temperature without heating to around the melting point of PHA, by adjusting the pH of an aqueous suspension containing PHA to fall within an acidic region. Accordingly, the present invention was accomplished.

The present invention relates to a method for producing PHA, including adjusting the pH of an aqueous PHA suspension to fall within an acidic region to obtain agglomerates of PHA.

According to the present invention, the acidic region is preferably a region of the pH being not less than 2.

According to the present invention, the amount of organic nitrogen present in the aqueous PHA suspension is preferably not greater than 6,000 ppm per weight of the PHA.

According to the present invention, a solvent included in the aqueous PHA suspension preferably contains water, an organic solvent that is miscible with water, or a mixed solvent of water and the organic solvent.

According to the present invention, PHA is preferably a copolymer constituted with two or more types of 3-hydroxyalkanoic acid selected from the group consisting of 3-hydroxypropionate, 3-hydroxybutyrate, 3-hydroxyvalerate, 3-hydroxyhexanoate, 3-hydroxyheptanoate, and 3-hydroxyoctanoate.

According to the present invention, PHA is preferably a binary copolymer of 3-hydroxyhexanoate and 3-hydroxybutyrate, or a ternary copolymer of 3-hydroxyhexanoate, 3-hydroxybutyrate and 3-hydroxyvalerate.

According to the present invention, PHA is preferably yielded using a microorganism.

According to the present invention, the microorganism belongs to genus *Aeromonas*, genus *Alcaligenes*, genus *Ralstonia*, or genus *Cupriavidus*.

According to the present invention, the microorganism is *Cupriavidus necator*.

Furthermore, the present invention relates to PHA agglomerates produced by the aforementioned method having an amount of organic nitrogen of not greater than 500 ppm.

The PHA agglomerates preferably have a volume mean particle diameter of not less than 20 µm.

Effects of the Invention

According to the present invention, PHA yielded by a microorganism can be purified not by an extraction operation with an organic solvent, and agglomeration of PHA is enabled at a temperature lower than the melting point of PHA without adding a third component such as a salt or a polymeric coagulant. PHA agglomerates with a fewer fine powders can be obtained with superior productivity while preventing contamination with constitutive components of cellular bodies. Thus obtained PHA agglomerates do not necessitate concerns about influences on quality which may be caused by adding a third substance, and lowering of the molecular weight of PHA by heating can be avoided.

MODE FOR CARRYING OUT THE INVENTION

The microorganism for use in the present invention is not particularly limited as long as is a microorganism that intracellularly produces PHA. A microorganism isolated from natural sources, a microorganism deposited with Microorganism Depositary (for example, IFO, ATCC, etc.), a variant or a transformant which can be prepared therefrom, or the like may be used. For example, bacteria of genus *Cupriavidus*, genus *Alcaligenes*, genus *Ralstonia*, genus *Pseudomonas*, genus *Bacillus*, genus *Azotobacter*, genus *Nocardia*, and genus *Aeromonas*, and the like may be involved. Of these, a microorganism belongs to genus *Aeromonas*, genus *Alcaligenes*, genus *Ralstonia*, or genus *Cupriavidus* is preferred. In particular, a strain of *Alcaligenes Lipolytica* (*A. lipolytica*), *Alcaligenes Latus* (*A. latus*), *Aeromonas Caviae* (*A. caviae*), *Aeromonas Hydrophila* (*A. Hydrophila*), *Cupriavidus necator* (*C. Necator*) or the like is more preferred, and *Cupriavidus necator* is most preferred. Also, when the microorganism does not originally have an ability to produce PHA or produces only a small amount of PHA, a synthase gene of intended PHA and/or a variant thereof may be introduced into the microorganism, and the resulting transformant may be used. Although the synthase gene of PHA which may be used in producing such a transformant is not particularly limited, a PHA synthase gene derived from *Aeromonas caviae* is preferred. By culturing these microorganisms under appropriate conditions, cellular bodies of a microorganism including PHA accumulated in cellular bodies can be obtained. Although the culture process is not particularly limited, for example, a process disclosed in JP-A No. H05-93049 or the like may be used.

PHA in the present invention is a generic name of a polymer constituted with 3-hydroxyalkanoic acid as a monomer unit. Although the constituting 3-hydroxyalkanoic acid is not particularly limited, specifically, a copolymer of 3-hydroxybutyrate (3HB) and other 3-hydroxyalkanoic acid, a copolymer of 3-hydroxyalkanoic acid including 3-hydroxyhexanoate (3HH), or the like may be exemplified. Furthermore, copolymers of two or more types of 3-hydroxyalkanoic acid selected from the group consisting of 3-hydroxypropionate, 3-hydroxybutyrate, 3-hydroxyvalerate, 3-hydroxyhexanoate, 3-hydroxyheptanoate and 3-hydroxyoctanoate as monomer units may be also exemplified. Among these, copolymers including 3HH as a monomer unit, for example, a binary copolymer (PHBH) of 3HB and 3HH (Macromolecules, 28, 4822-4828 (1995)), or a ternary copolymer (PHBVH) of 3HB, 3-hydroxyvalerate (3HV) and 3HH (Japanese Patent No. 2,777,757, JP-A No. H08-289797) are more preferred in light of physical properties of the resulting polyester. Herein, the composition ratio of each monomer unit constituting the binary copolymer of 3HB and 3HH, i.e., PHBH is not particularly limited; however, a composition ratio of 3HH unit being 1 to 99 mol %, preferably 1 to 50 mol %, and more preferably 1 to 25 mol % is suited, provided that the sum total of the entire monomer units is 100 mol %. In addition, the composition ratio of each monomer unit constituting the ternary copolymer of 3HB, 3HV and 3HH, i.e., PHBVH is not particularly limited; however, composition ratios suitably fall within the range of, for example, 3HB unit of 1 to 95 mol %, 3HV unit of 1 to 96 mol %, and 3HH unit of 1 to 30 mol %, respectively, provided that the sum total of the entire monomer units is 100 mol %.

Upon carrying out the agglomeration step in the present invention, an acid is added to an aqueous PHA suspension in order to adjust the pH of the aqueous PHA suspension to fall within an acidic region. The acid used for this purpose is not particularly limited and may be either an organic acid or an inorganic acid, and may or may not have volatility. Also, for example, either a strong acid such as sulfuric acid or hydrochloric acid, or a weak acid such as phosphoric acid or acetic acid may be used. In addition, upon agglomeration the pH of the aqueous PHA suspension is allowed to fall within a region of preferably the pH being not less than 2, more preferably the pH being not less than 3, and still more preferably the pH being not less than 4. Moreover, with respect to the upper limit of the preferable acidic region, the pH falls within a region of preferably the pH being not greater than 7, more preferably the pH being not greater than 6, and still more preferably the pH being not greater than 5. In addition, in order to make the resulting PHA agglomerates have a greater particle size, a heating operation may be performed in the agglomeration step. Although the heating temperature is not particularly limited, it is lower than the melting point of PHA, which is lower than the melting point of PHA preferably by at least 5° C., more preferably by at least 10° C., and still more preferably by 20 to 30° C. In order to inhibit lowering of the molecular weight of PHA, a lower temperature is desired. Specifically, the heating temperature is preferably not greater than 150° C., more preferably not greater than 120° C., and still more preferably not greater than 90° C. Although the lower limit of the heating temperature is not particularly limited, in order to produce agglomerates having a greater particle size, the lower limit is preferably not less than 20° C., and more preferably not less than 30° C. The time period required for elevating the temperature may vary depending on the apparatus size and capacity; however, it is necessary to heat enough until reaching the temperature at which agglomeration of PHA is effected and the particle size increased. The heating time period after reaching the aforementioned heating temperature is about 5 hrs or shorter, preferably 2 hrs or shorter, more preferably 1 hour or shorter, and still more preferably 30 min or shorter. Heating for at least 1 sec or longer is preferred. Also the concentration of PHA in the aqueous PHA suspension is not particularly limited, taking into consideration the influences of stirring and the like when stirred, the PHA concentration is preferably not greater than 40% by weight, more preferably not greater than 20% by weight, and still more preferably not greater than 10% by weight. The lower limit of the PHA concentration is not particularly limited; however, it is preferably not less than 1% by weight for efficiently executing agglomeration. These operations may be either continuous or batchwise. The aqueous suspension may or may not be stirred. The agglomeration as used herein means that the volume mean particle diameter of PHA particles becomes at least five times, desirably at least ten times, and more desirably at least 15 times with respect to the volume mean particle diameter of PHA before subjecting to the agglomeration operation.

The solvent included in the aqueous suspension in the present invention may include water, an organic solvent that is miscible with water, or a mixed solvent of water and the organic solvent. The organic solvent used may be only one type, or two or more types may be used in combination. In addition, the concentration of the organic solvent in the mixed solvent of water and the organic solvent is not particularly limited as long as it is not beyond the solubility of the organic solvent used in water. Furthermore, although the organic solvent that is miscible with water is not particularly limited, for example, alcohols such as methanol, ethanol, 1-propanol, 2-propanol, 1-butanol, 2-butanol, iso-butanol, pentanol, hexanol and heptanol, ketones such as acetone and methyl ethyl ketone, ethers such as tetrahydrofuran and dioxane, nitriles such as acetonitrile and propionitrile, amides such as dimethylformamide and acetamide, dimethyl sulfoxide, pyridine, piperidine, and the like may be exemplified. Among these, methanol, ethanol, 1-propanol, 2-propanol, 1-butanol, 2-butanol, iso-butanol, acetone, methyl ethyl ketone, tetrahydrofuran, dioxane, acetonitrile, propionitrile and the like are suited in light of favorable removability and the like. Still further, methanol, ethanol, 1-propanol, 2-propanol, 1-butanol, 2-butanol, iso-butanol, acetone and the like are more preferred in light of favorable availability. Still more preferred are methanol, ethanol and acetone. It should be noted that other solvent and/or components derived from the cellular bodies and compounds generated during purification may be contained as long as essential features of the present invention is impaired.

It is preferred that the amount of organic nitrogen in the aqueous PHA suspension is decreased by previously carrying out a step of degradation and/or removal of impurities included in the aqueous PHA suspension (particularly components other than PHA derived from an organism and components derived from the culture substrate) prior to the agglomeration step of allowing PHA to be aggregated by adjusting the pH of the aqueous PHA suspension to fall within the acidic region. Accordingly, PHA is efficiently aggregated in the agglomeration step that follows, and thus obtaining highly purified PHA is facilitated. A marker for degradation and/or removal of the impurities can be represented in terms of the amount of organic nitrogen per weight of PHA included in the aqueous PHA suspension. The amount of organic nitrogen is preferably not greater than 6,000 ppm, more preferably not greater than 4,000 ppm, more preferably not greater than 2,000 ppm, still more preferably not greater than 1,500 ppm, and most preferably not greater than 1,000 ppm per weight of the PHA.

Before degradation and/or removal of impurities of components other than PHA derived from an organism, and the like in the present invention, it is preferred that cells containing PHA are disrupted beforehand by a physical treatment, a chemical treatment or a biological treatment. Accordingly, a degradation and/or removal step that will follow can be efficiently performed. Although the disruption process is not particularly limited, any process carried out using fluid shearing force or solid shearing force, or by grinding, by means of a conventionally well-known French press, homogenizer, X-press, ball mill, colloid mill, DYNO mill, ultrasonic homogenizer or the like may be employed. Alternatively, a process in which an agent such as an acid, alkali, surfactant, organic solvent, cell wall synthesis inhibitor or the like is used, a process in which an enzyme such as lysozyme, pectinase, cellulase or zymolyase is used, a process in which supercritical fluid is used, an osmotic disruption process, a freezing process, a dry disruption process, and the like may be exemplified. Also, an autolysis process carried out using an action of protease, esterase, etc., included in the cells per se is also exemplified as one type of disruption process. In the foregoing disruption process, to select a process capable of inhibiting lowering of the molecular weight of PHA by a series of treatments is desired. In addition, these disruption processes may be used either alone, or a plurality of the processes may be used in combination. Also, either batchwise processing, or continuous processing may be conducted.

In general, an aqueous PHA suspension prepared by disrupting the PHA-containing cellular bodies according to the aforementioned process is contaminated with proteins, nucleic acids, lipids and sugar components in cells, and other constitutive components of cellular bodies, culture substrate residues, and the like. It is preferred to carry out a dehydration step for separating water containing these proteins and the like prior to the degradation and/or removal step described in the following. Accordingly, the amount of impurities included in the aqueous PHA suspension can be reduced, and thus the degradation and/or removal step can be efficiently carried out. Although dehydration process is not particularly limited, process of filtration, centrifugal separation, or precipitation separation may be exemplified. The concentration of PHA in the aqueous suspension subjected to the degradation and/or removal step is not particularly limited, which is preferably not less than 50 g/L, more preferably not less than 100 g/L, still more preferably not less than 200 g/L, and even more preferably not less than 300 g/L. In addition, the aforementioned dehydration step may be performed for the purpose of adjusting the concentration of PHA in the aqueous suspension.

The process of degradation and/or removal of impurities such as components other than PHA derived from the organism is not particularly limited, and for example, a process carried out using an enzyme may be exemplified. The enzyme which may be used includes a proteolytic enzyme, a lipolytic enzyme, cell wall degrading enzyme, nucleolytic enzyme, and the like. Specific examples of these enzymes include the followings. These may be used either alone, or two or more of these may be used in combination.

(1) Proteolytic Enzyme

Esperase, Alcalase, pepsin, trypsin, papain, chymotrypsin, aminopeptidase, carboxypeptidase, and the like (2) Lipolytic Enzyme lipase, phospholipase, cholineesterase, phosphatase, and the like (3) Cell Wall Degrading Enzyme lysozyme, amylase, cellulase, maltase, saccharase, α-glycosidase, β-glycosidase, N-glycosidase, and the like (4) Nucleolytic Enzyme ribonuclease, deoxyribonuclease, and the like The enzyme used in degradation of impurities such as components other than PHA derived from the organism is not limited to those described above, and may be an arbitrary enzyme having an activity of degradation of components derived from the organism as long as it can be used in industrial products. Also, a commercially available enzyme detergent used for washing or the like in general may be also used. Still further, an enzyme composition containing, for example, a stabilizing agent of an enzyme, an antisoil redeposition agent, etc., the enzyme is also acceptable, and it is not necessarily limited to use of only an enzyme. Preferable proteolytic enzymes which may be industrially used include, among the above-illustrated enzymes, protease A, protease P, protease N (all manufactured by Amano Enzyme inc.), Esperase, Alcalase, Savinase, Everlase (all manufactured by Novozymes A/S), and the like, and these can be suitably used also in light of the degradation activity, but not limited thereto.

The enzyme treatment is preferably carried out until a desired degree of the treatment is achieved, and the time period is usually 0.5 to 2 hrs. The amount of the enzyme to be used depends on the type and activity of the enzyme, and is not particularly limited, which is preferably 0.001 to 10 parts by weight, and in light of the cost, more preferably 0.001 to 5 parts by weight relative to 100 parts by weight of PHA.

Other process for the degradation of impurities such as components other than PHA derived from the organism includes a process in which hypochlorous acid or hydrogen peroxide is used. When hypochlorous acid is used, the pH of the system is adjusted to fall within an alkaline region, and the degradation is executed under conditions in which heat, light, or contact with metal can be inhibited, whereby PHA having a low amount of remaining chlorine can be obtained. The pH is desirably not less than 8, more desirably not less than 10, and still more desirably not less than 12. The treatment temperature is desirably not greater than 40° C., more desirably not greater than 30° C., still more desirably not greater than 20° C., and for surely achieving the effects, the treatment is carried out at not greater than 10° C.

As described above, in the aforementioned dehydration step, for separating PHA from water containing impurities such as other components derived from the organism, filtration, centrifugal separation or the like may be carried out. Although the filtration process is not particularly limited, a process carried out using Nutsche or the like, or process such as suction filtration or pressure filtration is desired. For industrial applications, filtration equipment having a compressing function such as a filter press, tube press, plate press, gauge press, belt press, screw press or disk press, as well as a centrifugal dehydrator, a multiple cylindrical filtration element or the like may be selected. When improving productivity is intended, continuous type such as a multiple cylindrical filtration element is desired. As a process for removing scums of particles in a continuous type filtration element, a string system, a scraper system, a precoating scraper system or the like may be involved. Alternatively, a membrane separation system may be also employed. As a process for filtration involving membrane separation, dead end filtration, or cloth flow filtration may be selected. Any case may be selected based on the filterability, the extent of clogging of the filter material, membrane and the like. In addition, reduced pressure or vacuum may be provided, or compression may be permitted. Furthermore, a process in which centrifugal force is employed may be used. As a filter material, any of a variety of materials such as a paper, woven fabric, nonwoven fabric, screen, sintered plate, unglazed pottery, polymer membrane, punching metal or wedge wire may be selected. Any one may be selected depending upon the productivity and degree of clogging and the like. Also, a filter aid may or may not be used. When a filter aid is used, either a process of precoating the filter aid onto the filter material beforehand (i.e., precoating system), or a process of previously adding to a liquid subjected to the filtration (i.e., body feeding method) may be employed.

Although the process of centrifugal separation in the aforementioned dehydration step is not particularly limited, a centrifugal settler, a centrifugal dehydrator or the like may be used. In the case of a centrifugal settler, a separator type, a cylindrical type, and a decanter type may be exemplified. In the case of the separator type, a disk type, a self cleaning type, a nozzle type, a screw decanter type, a skimming type, and the like may be exemplified. Depending on the procedure of discharging precipitated components, there are batch type and continuous type, respectively. Also, with respect to the centrifugal dehydrator, there may be batch type and continuous type. Separation of precipitates containing PHA from culture liquid components is enabled with these equipments, based on the difference in specific gravity.

Other process which may be used in the above dehydration step may include a floatation process, an electrophoresis process, a cyclone processing, and the like. The processes of filtration and centrifugal separation, as well as floatation may be used alone, or in combination.

After PHA was recovered by the process such as filtration and/or centrifugal separation in the aforementioned dehydration step, the recovered PHA is washed with water or the like, whereby further purified PHA can be obtained. The washing may be carried out using not only water but also an organic solvent, and water and an organic solvent may be used as a mixture. Also, the pH of water may be adjusted. When an organic solvent is used as a washing solvent, preferably, a hydrophilic solvent, and more specifically methanol, ethanol, acetone, acetonitrile, tetrahydrofuran, a ketone, an amine or the like may be used. In addition, a surfactant or the like may be added to water. A plurality of types of these organic solvents and water may be used as a mixture. Moreover, water or the organic solvent may be heated or sprayed in the form of vapor to improve the washing property as long as this process is carried out within a short period of time.

As explained in the foregoing, according to the most suitable aspect of the present invention, agglomerates of PHA can be efficiently produced by sequentially carrying out: a culture step of culturing a microorganism having an ability to intracellularly produce PHA; a disruption step of disrupting the microorganism containing PHA; a dehydration step of separating water from an aqueous suspension containing thus disrupted microorganism; a purification step of degradation and/or removal of impurities; a washing step of washing PHA; and agglomeration step of adjusting the pH of the resulting aqueous PHA suspension to an acidic region to obtain PHA agglomerates. However, the present invention does not necessarily require carrying out all the steps described above.

By carrying out the agglomeration step of the present invention in this manner after carrying out the purification step of degradation and/or removal of impurities derived from the cellular bodies and the culture substrate, and/or washing step, highly purified PHA agglomerates can be obtained. Also, by further washing the obtained agglomerates in the washing process as described above as needed, still further purified PHA agglomerates can be obtained.

From the foregoing, production of PHA agglomerates having an amount of organic nitrogen of not greater than 500 ppm, preferably not greater than 400 ppm, more preferably not greater than 300 ppm, still more preferably not greater than 200 ppm, and particularly preferably not greater than 100 ppm is enabled. In addition, from the foregoing, obtaining PHA agglomerates with a fewer fine powders is enabled. Thus obtained PHA agglomerates have a volume mean particle diameter of preferably not less than 20 μm, more preferably not less than 30 μm, and still more preferably not less than 100 μm. Although the upper limit is not particularly limited, PHA agglomerates having a volume mean particle diameter of not greater than about 5,000 μm can be obtained according to the present invention.

The PHA agglomerates produced in this manner having a low organic nitrogen content can be easily processed also in light of the volume mean particle diameter. Furthermore, also due to including a lower amount of impurities, a variety of applications, for example, not only for commodity items such as films and bottles, but a wide range of applications also in medical use can be expected since it has low allergenicity.

Hereinafter, the present invention is explained in more detail by way of Examples in the following, but the present invention is not limited only to these Examples.

(Process for Determining Amount of Organic Nitrogen in Aqueous PHA Suspension (Per Weight of PHA))

The entirety of a water soluble solvent in an aqueous PHA suspension was evaporated to obtain a residual solid content. To this solid content was added 5M NaOH, and a hydrolysis reaction was carried out at 95° C. This hydrolysis liquid was neutralized with the equivalent amount of a 60% aqueous acetic acid solution, and thereto were added an acetate buffer and a ninhydrin solution to allow a color reaction at 100° C. The absorbance of this color reaction liquid was measured with a ratio beam spectrophotometer model U-1800 manufactured by Hitachi, Ltd. By comparing this absorbance with a calibration curve produced using a leucine sample, the amount of organic nitrogen in the solid content was calculated. The amount of organic nitrogen in the aqueous PHA suspension (per weight of PHA) was determined in terms of the amount of organic nitrogen per weight of the solid content.

(Process for Determining Amount of Organic Nitrogen in PHA Agglomerates (Per Weight of PHA))

To PHA agglomerates was added 5M NaOH, and a hydrolysis reaction was carried out at 95° C. This hydrolysis liquid was neutralized with the equivalent amount of a 60% aqueous acetic acid solution, and thereto were added an acetate buffer and a ninhydrin solution to allow a color reaction at 100° C. The absorbance of this color reaction liquid was measured with a ratio beam spectrophotometer model U-1800 manufactured by Hitachi, Ltd. By comparing this absorbance with a calibration curve produced using a leucine sample, the amount of organic nitrogen in the PHA agglomerates was calculated. The amount of organic nitrogen in the PHA agglomerates (per weight of PHA) was determined in terms of the amount of organic nitrogen per weight of the PHA agglomerates.

Example 1

Preparation of Cell Culture Liquid

*Ralstonia eutropha* KNK-005 strain disclosed in paragraph No. of PCT International Publication No. 2008/010296 was cultured according to a process disclosed in paragraph Nos. [0050]-[0053] of the same document to obtain a cell culture liquid including cellular bodies containing PHA. Note that *Ralstonia eutropha* is classified as *Cupriavidus necator* at present.

Example 2

Sterilization Process

The cell culture liquid obtained in Example 1 was subjected to a treatment of heating with stirring at an internal temperature of 60 to 80° C. for 20 min to execute a sterilization treatment.

Example 3

To the sterilized cell culture liquid obtained in Example 2 was added 0.2% by weight sodium dodecyl sulfate. Furthermore, after adding sodium hydroxide such that the pH became 11.0, the mixture was incubated at 50° C. for 1 hour. Thereafter, disruption at high pressure was carried out with a homogenizer at high pressure (model PA2K manufactured by Niro Soavi S.P.A) at a pressure of 450 to 550 kgf/cm².

To the disruption liquid after subjecting to disruption at high pressure was added an equal amount of distilled water. Thereafter, the disruption liquid after the disruption at high pressure was subjected to centrifugal separation, followed by eliminating the supernatant (×3 concentrated). To the ×3 concentrated aqueous suspension of PHA was added water in an equal amount to the eliminated supernatant, followed by permitting suspension. Thereto were added 0.2% by weight sodium dodecyl sulfate, and protease in an amount of 1/100 by weight of PHA (manufactured by Novozymes A/S, Esperase), and the mixture was stirred for 2 hrs while maintaining the pH of 10 at 50° C. Thereafter, the PHA concentration was adjusted to 10% by weight. The amount of organic nitrogen present in the obtained aqueous PHA suspension was 3,415 ppm per weight of PHA.

The pH of this aqueous PHA suspension was adjusted to 3, 4, 5, 6 or 7 with sulfuric acid, and the temperature was adjusted to 30° C., 50° C. or 70° C. while stirring to permit agglomeration. The heating time period was 60 min. The volume mean particle diameter of thus resulting agglomerates was determined using a particle size analyzer (manufactured by Shimadzu Corporation, model SALD-300V). The results are shown in Table 1. Accordingly, it was proven that PHA became more likely to be aggregated even at lower temperatures as the pH of the aqueous PHA suspension was more strongly acidic.

TABLE 1

|  | pH 3 | pH 4 | pH 5 | pH 6 | pH 7 |
| --- | --- | --- | --- | --- | --- |
| 30° C. | 17.1 μm | 14.5 μm | 13.3 μm | 3.3 μm | 1.5 μm |
| 50° C. | 30.2 μm | 28.5 μm | 30.5 μm | 31.0 μm | 1.5 μm |
| 70° C. | 283.6 μm | 280.1 μm | 263.9 μm | 241.3 μm | 210.3 μm |

Example 4

To the sterilized cell culture liquid obtained in Example 2 was added 0.2% by weight sodium dodecyl sulfate. Furthermore, after adding sodium hydroxide such that the pH became 11.0, the mixture was incubated at 50° C. for 1 hour. Thereafter, disruption at high pressure was carried out with a homogenizer at high pressure (model PA2K manufactured by Niro Soavi S.P.A) at a pressure of 450 to 550 kgf/cm².

To the disruption liquid after subjecting to disruption at high pressure was added an equal amount of distilled water. Thereafter, the disruption liquid after the disruption at high pressure was subjected to centrifugal separation, followed by eliminating the supernatant (×2 concentrated). To the ×2 concentrated aqueous suspension of PHA was added water in an equal amount to the eliminated supernatant, and the mixture was subjected to centrifugal separation. After the supernatant was eliminated, water was added again, followed by permitting suspension. Thereto were added 0.2% by weight sodium dodecyl sulfate, and protease in an amount of 1/100 by weight of PHA (Novozymes A/S, Esperase), and the mixture was stirred for 2 hrs while maintaining the pH of 10 at 50° C. Thereafter, the PHA concentration was adjusted to 10% by weight. The amount of organic nitrogen present in the obtained aqueous PHA suspension was 5,486 ppm per weight of PHA.

The pH of this aqueous PHA suspension was adjusted to 4 with sulfuric acid, and the temperature was adjusted to 70° C. while stirring to permit agglomeration over 30 min. The volume mean particle diameter of thus resulting agglomerates was determined using a particle size analyzer (manufactured by Shimadzu Corporation, model SALD-300V). Consequently, the volume mean particle diameter before subjecting to the agglomeration operation was 1.5 μm, whereas the volume mean particle diameter after the agglomeration operation was 218.2 μm. Furthermore, the obtained agglomerates were washed with alkaline water having a pH of 11.5 and methanol. The amount of organic nitrogen of the PHA agglomerates after washing was 426 ppm per PHA. Accordingly, PHA agglomerates having the amount of organic nitrogen of not greater than 500 ppm was successfully obtained.

The invention claimed is:

1. A method for producing poly-3-hydroxyalkanoic acid agglomerates, the method comprising
   culturing a microorganism having an ability to intracellularly produce poly-3-hydroxyalkanoic acid;
   purifying poly-3-hydroxyalkanoic acid in the absence of any organic solvent by degradation and/or removal of impurities to obtain an aqueous poly-3-hydroxyalkanoic acid suspension having an amount of organic nitrogen of not greater than 6,000 ppm per weight of the poly-3-hydroxyalkanoic acid,
   allowing poly-3-hydroxyalkanoic acid to be aggregated by adjusting the pH of the aqueous poly-3-hydroxyalkanoic acid suspension to fall within an acidic region after purifying poly-3-hydroxyalkanoic acid by degradation and/or removal of impurities to obtain poly-3-hydroxyalkanoic acid agglomerates.

2. The method for producing poly-3-hydroxyalkanoic acid agglomerates according to claim 1, wherein the acidic region is a region of the pH being not less than 2.

3. The method for producing poly-3-hydroxyalkanoic acid agglomerates according to claim 2, wherein the acidic region is a region of the pH being not less than 3.

4. The method for producing poly-3-hydroxyalkanoic acid agglomerates according to claim 1, wherein the amount of organic nitrogen present in the aqueous poly-3-hydroxyalkanoic acid suspension is not greater than 4,000 ppm per weight of the poly-3-hydroxyalkanoic acid.

5. The method for producing poly-3-hydroxyalkanoic acid agglomerates according to claim 1, wherein the solvent included in the aqueous poly-3-hydroxyalkanoic acid suspension comprises water, an organic solvent that is miscible with water, or a mixed solvent of water and the organic solvent.

6. The method for producing poly-3-hydroxyalkanoic acid agglomerates according to claim 1, wherein the poly-3-hydroxyalkanoic acid is a copolymer constituted with two or more types of 3-hydroxyalkanoic acid selected from the group consisting of 3-hydroxypropionate, 3-hydroxybutyrate, 3-hydroxyvalerate, 3-hydroxyhexanoate, 3-hydroxyheptanoate, and 3-hydroxyoctanoate.

7. The method for producing poly-3-hydroxyalkanoic acid agglomerates according to claim 6, wherein the poly-3-hydroxyalkanoic acid is a binary copolymer of 3-hydroxyhexanoate and 3-hydroxybutyrate, or a ternary copolymer of 3-hydroxyhexanoate, 3-hydroxybutyrate and 3-hydroxyvalerate.

8. The method for producing poly-3-hydroxyalkanoic acid agglomerates according to claim 1, wherein the microorganism is a microorganism belonging to genus *Aeromonas*, genus *Alcaligenes*, genus *Ralstonia*, or genus *Cupriavidus*.

9. The method for producing poly-3-hydroxyalkanoic acid agglomerates according to claim 8, wherein the microorganism is *Cupriavidus necator*.

10. The method for producing poly-3-hydroxyalkanoic acid agglomerates according to claim 1, wherein the microorganism is a transformant.

11. The method for producing poly-3-hydroxyalkanoic acid agglomerates according to claim 10, wherein the microorganism is a transformant into which at least one selected from a poly-3-hydroxyalkanoic acid synthase gene derived from *Aeromonas caviae* and a variant thereof was introduced.

12. The method for producing poly-3-hydroxyalkanoic acid agglomerates according to claim 2, wherein the solvent included in the aqueous poly-3-hydroxyalkanoic acid suspension comprises water, an organic solvent that is miscible with water, or a mixed solvent of water and the organic solvent.

13. The method for producing poly-3-hydroxyalkanoic acid agglomerates according to claim 3, wherein the solvent included in the aqueous poly-3-hydroxyalkanoic acid suspension comprises water, an organic solvent that is miscible with water, or a mixed solvent of water and the organic solvent.

14. The method for producing poly-3-hydroxyalkanoic acid agglomerates according to claim 4, wherein the solvent included in the aqueous poly-3-hydroxyalkanoic acid suspension comprises water, an organic solvent that is miscible with water, or a mixed solvent of water and the organic solvent.

15. The method for producing poly-3-hydroxyalkanoic acid agglomerates according to claim 1, wherein the poly-3hydroxyalkanoic acid agglomerates have an amount of organic nitrogen of not greater than 500 ppm.

* * * * *